United States Patent [19]

Sandhu

[11] 4,393,712
[45] Jul. 19, 1983

[54] PORTABLE LIQUID CRYSTAL TESTING DEVICE

[75] Inventor: Jaswinder S. Sandhu, Chicago, Ill.

[73] Assignee: Raj Technology Partnership, Chicago, Ill.

[21] Appl. No.: 300,003

[22] Filed: Sep. 8, 1981

[51] Int. Cl.³ .............................................. G01N 29/00
[52] U.S. Cl. ........................................ 73/603; 128/660
[58] Field of Search .................. 73/603, 606, 607, 624, 73/628, 655; 128/660

[56] References Cited

U.S. PATENT DOCUMENTS

| 4,038,865 | 8/1977 | Flambard et al. | 73/628 |
| 4,116,074 | 9/1978 | Jensen | 73/607 |
| 4,338,821 | 7/1982 | Dion | 73/603 |

Primary Examiner—Stephen A. Kreitman
Attorney, Agent, or Firm—Gerald S. Geren

[57] ABSTRACT

There is disclosed herein a portable device for inspecting bodies for internal flaws or other internal features. The device is constructed so as to be mounted on the surface of the body, emit and receive ultrasonic energy, and display the same on a liquid crystal display. The device includes a first housing member for supporting a transducer in relation to the surface being inspected. The device also includes a second housing member for supporting and positioning the liquid crystal display in relation to the surface and in relation to the transducer. Interconnecting means are provided for adjustably interconnecting the two members and fixing their positions in a reflection-receiving relation. The liquid crystal support housing is a substantially hollow tubular member having a viewing end and a surface contacting end. The liquid crystal display is positioned intermediate the ends. The contacting surface is constructed to be acoustically coupled to the surface of the body and variable focal length ultrasonic lens is positioned between the coupling and liquid crystal display with acoustic transmission means being provided for transmitting sonic energy from the surface through the lens and to the display where it can be viewed. Optical enhancement means are provided at the viewing end of the housing for assuring a suitable visual image on the display.

8 Claims, 4 Drawing Figures

PORTABLE LIQUID CRYSTAL TESTING DEVICE

BACKGROUND OF THE INVENTION

This invention relates to an apparatus and method for non-destructively inspecting various bodies for discontinuities, such as flaws or internal features such as organs in the human body.

It is known that ultrasonics can be utilized for detecting flaws using conventional pulse echo techniques. As a result, portable thickness meters, flaw detectors, etc., are now available. Some of these devices employ extensive and expensive electronic circuitry to scan a body and build up an electronic image. However, these devices do not enable the user to readily and economically visualize the flaw as a picture.

Furthermore, there has recently been developed and disclosed a technique for inspecting bodies which are immersed in a liquid medium, by passing ultrasonic energy through the object to be examined and receiving that energy on a liquid crystal display.

U.S. patent application, Ser. No. 232,247, filed Feb. 6, 1981 discloses such a device. That devices includes an improved liquid crystal cell for receiving and displaying the ultrasonic energy.

Disclosures concerning ultrasonic techniques in general include Gooberman's text entitled *Ultrasonics Theory and Application,* published by E. U. P. Limited §11 "Miscellaneous Applications on Ultrasonics", subsection 1.2 "Flaw Detection". Disclosures relating to liquid crystals may be found in the publication by E. Merck or Darmstadt, Germany, entitled Licristal—Liquid Crystals; and in texts by de Genness, *Physics of Liquid Crystals,* Oxford University Press, 1974, and S. Chandrasekar, *Liquid Crystals,* Cambridge University Press, 1978. Reference is also made to "Acousto-Hydrodynamics Effects In Liquid Crystals" authored by J. S. Sandhu, W. G. B. Britton and R. W. B. Stephens, Physics Department, Chelsea College, London, United Kingdom. Finally, there are several patents which deal with related ultrasonic technology. See for example, Dreyer, U.S. Pat. No. 3,597,954; Kessler, U.S. Pat. No. 3,707,323; Gregus, U.S. Pat. No. 3,831,434; and Brenden, U.S. Pat. No. 3,879,989.

However, none of these references solve the problem of inspecting a large body, which cannot be immersed in a liquid bath, for internal flaws or features, and for providing a visual picture of those flaws or features.

It is therefore the object of this invention to provide a portable device which permits inspection of large bodies for internal flaws or features without immersing the body in a liquid bath and which provides a visual image of the flaw.

Furthermore, one of the problems in the medical field has been to provide a suitable non-invasive diagnostic technique for internal human examination. Presently ultrasonics is used for internal human examination, but the apparatus which is used is large, includes extensive costly electronics, and is not portable. Thus the patient must be brought to the ultrasonic testing device rather than the device being carried by a physician to the patient. Moreover, the electronics is required to provide a visual image of the area being examined due to the present state of the technology.

It is therefore an object of this invention to provide a portable ultrasonic device which permits internal human examination and which can be carried by a physician to the patient.

These and other objects of the invention will become apparent from the following specification and appended claims.

SUMMARY OF THE INVENTION

There is provided by this invention a portable flaw detecting device which employs a liquid crystal display cell. The device includes an ultrasonic transducer and liquid crystal display cell which receives reflected or scattered ultrasonic energy and displays the flaws or features which are detected.

More particularly, the device includes a first housing having a transducer support member for supporting the transducer in relation to the surface of the object to be examined. A second housing is provided and includes a liquid crystal display support for positioning and supporting the liquid crystal cell in relation to the surface. Interconnecting means are provided for interconnecting the two housing members in adjustable and angular relation to each other. The angular relationship generally is selected so as to receive reflected or scattered energy from the body.

The liquid crystal support member is a generally elongated hollow tubular member having a viewing end and a surface contact end. The liquid crystal display cell is positioned intermediate the ends. The surface contacting end is provided with an acoustical coupler (e.g., acoustical matching layers) which permits the reflected or scattered energy to be efficiently received by the liquid crystal cell. A liquid coupling medium is positioned between the coupler and the liquid crystal cell, and, if necessary, a variable focal length acoustic lens is also provided. Appropriate illumination is also provided in the system.

It has been found that using this system permits inspection of large bodies, which cannot be readily immersed, for flaws and features, as well as for inspecting the human body. It is anticipated that this device will find a number of uses for physiological examination.

As described hereinafter, these devices include a liquid crystal cell having a particular laminated construction and the coupling medium is important depending upon the material or body to be examined.

DESCRIPTION OF THE PREFERRED EMBODIMENT

Figure 1:
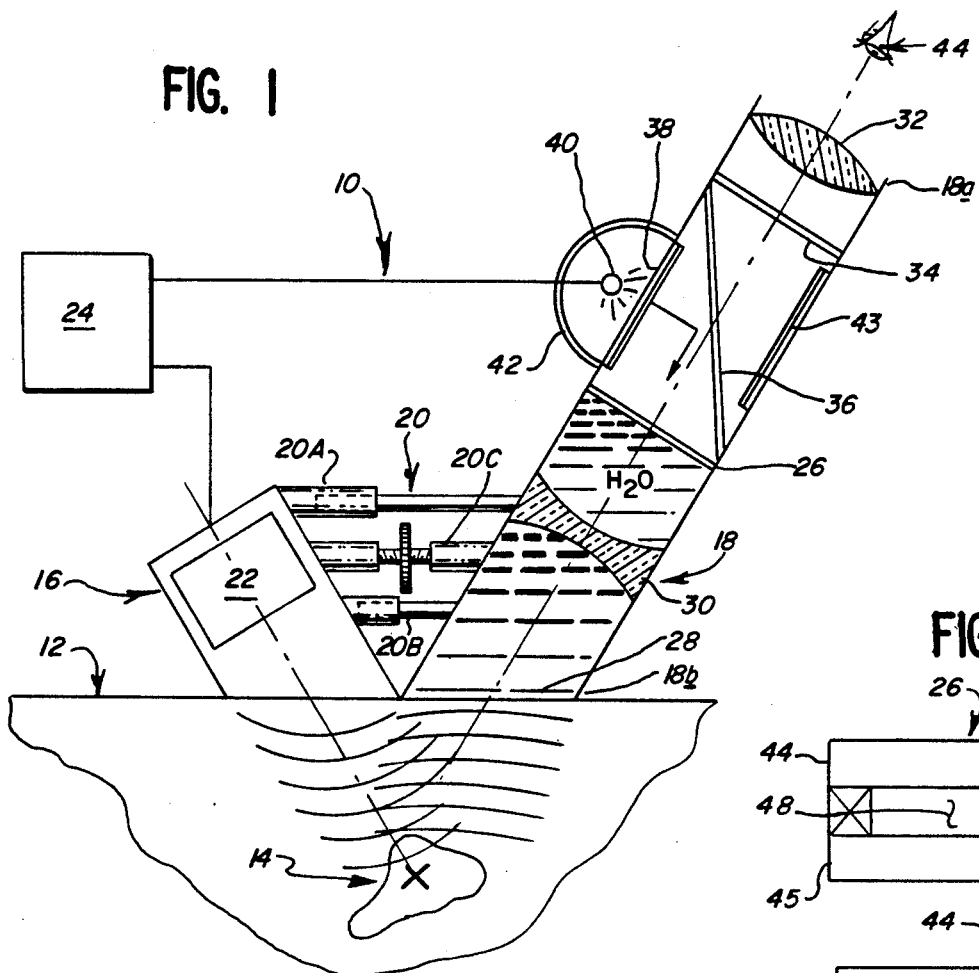
FIG. 1 is a sectional view showing a portable display device of a type suitable for use in connection with inspecting for internal flaws on large bodies.

Referring now to FIG. 1, there is shown a portable testing device 10 generally, which is shown resting on the surface of a large, rigid body 12, which has an interior flaw 14.

The device 10 includes three main assemblies, which are the transducer housing 16, liquid crystal housing 18, and the interconnecting member 20.

The transducer housing 16 supports therein a standard ultrasonic transducer 22 which is powered by the supply 24. In addition to standard transducers, transducer arrays which can provide beam steering can be used. The housing 16 orients the transducer so that the transducer's radiation axis is at an angle with respect to the surface 12.

The liquid crystal display housing 18 includes a viewing end 18a and a contact end 18b.

A multi-layer liquid crystal display cell 26 is fixedly secured in the tubularly-shaped support housing 18 intermediate the ends 18a and 18b.

The contacting end 18b includes an acoustic coupling member 28 which is adapted to contact the surface 12 and acoustically couple thereto so as to minimize acoustic losses between the surface 12 and housing 18.

The device as shown includes a variable focal length acoustic lens 30 which is positioned between the coupler 28 and the liquid crystal display 26. The coupler, lens and display are acoustically coupled to each other through a liquid medium which fills the space between (1) the coupler and lens and (2) the lens and display.

The display 26 is viewed from the viewing end 18a. A reflected light system is shown for enhancing the image on the display. However, as described hereinafter, a transmitted light system may also be used. The reflected light system includes an objective lens 32, a polarizer 34, a half-silvered mirror 36, a polarizer 38, and a light source 40.

A concave reflecting mirror arrangement 42 and a black, light-absorbing surface 43 are provided on opposite sides of the housing 18.

Details of the liquid crystal cell 26 and coupling member 28 will be described hereinafter.

The interconnecting means 20 is provided for adjustably interconnecting and fixing the relative positioning of the transducer housing relative to the liquid crystal housing 18. It could generally be stated that the interconnecting means can be used to assure the relative positioning of the transducer and liquid crystal cell in a reflection-receiving relationship.

The interconnecting member 20 includes an upper slide 20a and a lower slide 20b. Intermediate the slides is a thumb screw adjuster 20c which includes a pair of oppositely threaded members that can be operated by a thumb screw to controllably move the housings 16 and 18 together and apart. In this embodiment the housing members are moved linearly with respect to each other.

In operation the transducer 22 emits ultrasonic energy which passes through body 12 and strikes the flaw 14. The energy striking the flaw 14 is reflected or scattered in many directions, but some energy is directed toward the liquid crystal cell 26. That energy passes to the coupling member 28 and into the transmitting medium in contact therewith. The lens 30 is then used to focus the energy onto the liquid crystal cell 26.

An image is then formed by the interaction of the ultrasonic energy and the liquid crystal molecules in the cell.

The image on the cell is viewed by illuminating the surface of the cell via the lamp 40 and half-silvered or semi-reflecting mirror 36. The image can thus be seen by the viewer 41, through the lens 32, through polarizer 34, and through the half-silvered mirror 36.

Figure 2:
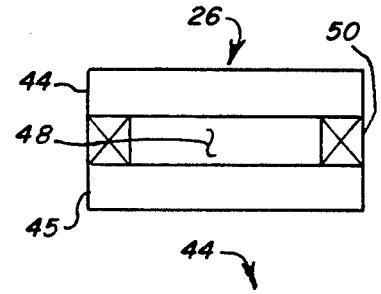
FIG. 2 is a sectional view showing the construction of a liquid crystal display cell.

Referring now to the liquid crystal display 26, the display includes, as shown in FIG. 2, two covers 44 and 45, each of which are acoustically transparent, rigid and at least one of which is optically transparent. A liquid crystal material 48 is positioned between the covers 44 and 45 and sealed in place by the use of a peripheral spacer 50.

The preferred liquid crystal material used in the cell herein is of the nematic type which is homeotropically aligned (i.e., the molecules are on average normal to the cover surfaces).

It is also desirable that the cell be as transparent to the sonic energy as possible. In other words, sonic energy striking the surface of the cover 45 and transmitted through the entire call should be maximized and absorption and internal reflection minimized, since they will degrade the image quality. It is also desirable that the acoustic properties of the cell be very similar to the properties of the surrounding medium, which in this case is water on one side and air on the other side. However, the cell should also be useful with water/water interfaces.

It has been determined that if the thickness of the cover is much much less than one-fourth of the wavelength of the sound wave propagating through the cover (i.e., WL/4), then thickness effects relating to the sonic absorption could be ignored for analytical purposes at normal incidence (i.e., the ultrasonic beam is perpendicular to the cover). For the optically transparent cover 45, glass has been used although other transparent materials may be used.

It has been found that glass slides or panes which are available in thickness of 200 micrometers or less are sufficient to avoid any considerations concerning absorption or reflection. However, such thin slides are very flexible and would not assure proper alignment of the liquid crystal molecules in uniform thickness of a liquid crystal layers.

It has been found that in order to provide the desired rigidity, the glass cover must be of a laminated structure having at least two glass panes.

Figure 3:
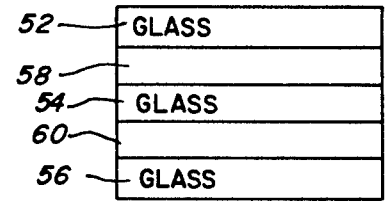
FIG. 3 is a sectional view showing a laminated structure for transmitting acoustic energy.

In FIG. 3 a five-layer thick glass cover is shown. There are provided three glass layers 52, 54, and 56 and two intermediate adhesive layers 58 and 60. It is desirable that each of the layers be of a thickness much much less than WL/4 for the appropriate material so that for absorption purposes the individual thicknesses can be ignored. The question then is: What is the acoustic impedance of the composite structure? A calculation based on the empirically determined formula:

$$1/Zc = 1/Zg = 1/Za = 1/Zg = 1/Za = 1/Zg$$

can be used. ZC is the impedance of composite, Zg is the impedance of glass, and Za is the impedance of the adhesive which is estimated to be similar to the impedance of Plexiglas or Lucite.

Laminated structures described above can be successfully employed in cell 26 for both covers.

In addition, the acoustic coupling member 28 can be provided of a similar laminated structure which assures proper acoustic matching between the surface of the body to be examined and the acoustic medium which is carrying the signal to the display cell.

Figure 4:
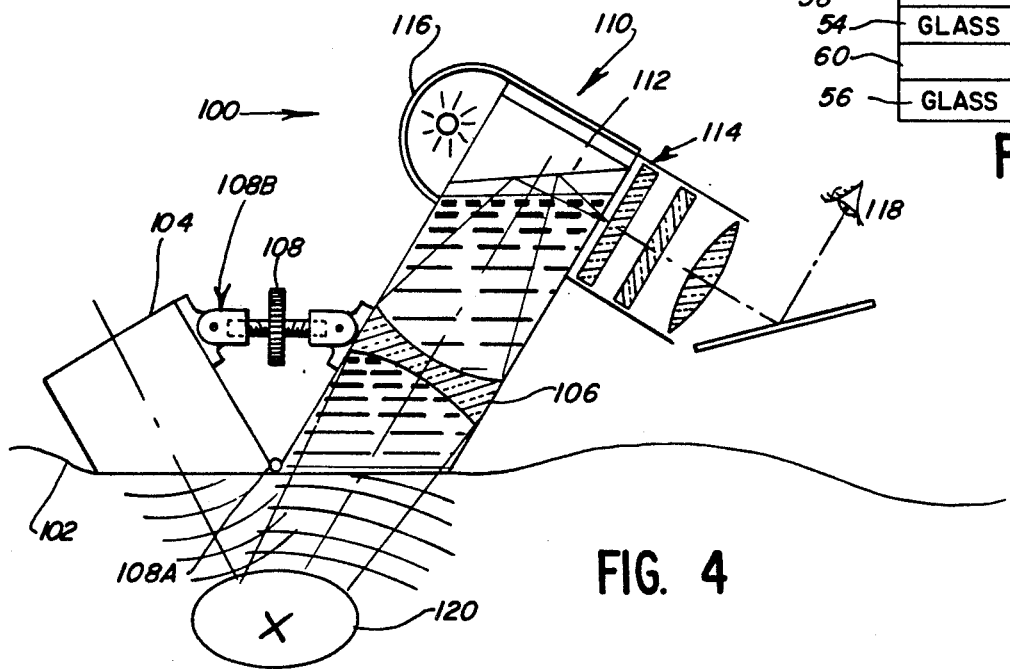
FIG. 4 is a sectional view showing a device for use in examining human bodies.

Referring now to FIG. 4, another embodiment 100 of the portable tester is shown. The tester 100 is similar to the tester shown in FIG. 1, except that it includes a transmissive optical system rather than reflective, but it should be appreciated that transmissive or reflective systems are similar and either can be selected based upon factors such as end use, ease of operation, etc.

Furthermore, the tester 100 is shown resting on a soft surface 102, such as a human body, and is useful in examining internal organs or for tumors and the like.

Referring now to FIG. 4, there is shown a transducer housing 104, and a liquid crystal display housing 106, each of which are similar to the corresponding parts in FIG. 1, as well as interconnecting means 108. The interconnecting means 108 provides a pivoting motion so as to permit adjustment to soft surfaces. The interconnecting means includes a pivot point 108a, such as a hinge, that connects the two housings at their lower ends and a thumb wheel assembly 108b that also pivotally connects the housings and by a pair of oppositely threaded members that permits the housings to be drawn together or separated. Of course depending upon the end use, the pivoting interconnection and the linear interconnection can be used interchangeably.

The principal difference relates to the optical system 110 generally, which is of the transmissive type. In this system, there is provided an acoustic reflector 112 which directs acoustic energy to the display cell 114 in the side of the housing. The specific construction for the reflector is disclosed in patent application, Ser. No. 232,247. The acoustic reflector is optically transparent and light from the source 116 passes through the acoustic reflector 112, illuminates and passes through the liquid crystal display cell. Appropriate polarizers and reflectors are provided so that the image on the cell can be seen by the viewer 118.

This type of device can be used for physiological examination. For example, a tumor, such as 120, can be located and viewed using this device, in the same manner as internal flaws can be located. Internal organs can also be located.

It will be appreciated that numerous changes and modifications can be made to the devices disclosed herein without departing from the spirit and scope of this invention.

What is claimed and desired to be secured by Letters Patent of the United States is:

1. A portable device for inspecting bodies for internal flaws and for providing a visual image thereof which comprises:
   an ultrasonic transducer which emits ultrasonic energy for insonifying at least a portion of the body to be inspected;
   a liquid crystal display for receiving energy from the insonified body and for visually displaying an image thereof; and
   means for viewing the display;
      wherein the improvement comprises said device being constructed to rest on a surface, to be acoustically coupled to said surface, and to inspect for flaws or features beneath said surface, said device including:
   an assembly for separately but adjustably supporting said transducer and said liquid crystal display in reflection-receiving relation to each other, said assembly including:
   first housing means for supporting said transducer in relation to said surface;
   second housing means for supporting said display in relation to said surface; and
   interconnecting means for adjustably interconnecting said first housing means and said second housing means in reflection-receiving relation to each other,
   said second housing means including:
   an elongated hollow tube with one end constructed to contact said surface and the other end constructed for viewing, with the liquid crystal display being positioned intermediate the ends of the second housing means, there being further provided:
   means at the viewing end for optically viewing images developed by said display;
   means at the contacting end for acoustically coupling said second housing means to the surface; and
   acoustic transmission means for contacting the cell and the coupling means for carrying acoustic signals from the contact end of said housing to the cell;
   whereby when said device is placed on a surface, ultrasonic energy emitted from said transducer is projected into the body and reflections therefrom are received on said display through said coupling end and transmission medium for optical viewing.

2. A device as in claim 1, wherein said interconnecting means is adjustable so as to permit relative angular adjustment of the first and second housings for maximizing acoustic signal reception.

3. A device as in claim 1, wherein there is further provided an acoustic lens for focusing ultrasonic energy on said liquid crystal display.

4. A device as in claim 1, wherein said liquid crystal display is positioned within said second housing means and is positioned generally normal to the tube axis.

5. A device as in claim 1, wherein said liquid crystal display is positioned within a side wall of said second housing means.

6. A device as in claim 1, wherein there is further provided means for optically enhancing the image on said liquid crystal display.

7. A device as in claim 6, wherein said optical enhancement means includes a reflected light system for directing light from a source.

8. A device as in claim 6, wherein the optical enhancement means includes a transmitted light system for directing light from a source through the liquid crystal display to a viewer.

* * * * *